(12) United States Patent
Schmit et al.

(10) Patent No.: US 7,465,824 B2
(45) Date of Patent: Dec. 16, 2008

(54) PROCESS FOR THE PRODUCTION OF HIGH PURITY AROMATIC CARBOXYLIC ACIDS USING A BENZOIC ACID AND WATER SOLVENT FOR OXIDATION AND PURIFICATION

(75) Inventors: Carolyn E. Schmit, Naperville, IL (US); David L. Sikkenga, Wheaton, IL (US); Christopher G. Meller, Carol Stream, IL (US)

(73) Assignee: BP Corporation North America Inc., Warrenville, IL (US)

( * ) Notice: Subject to any disclaimer, the term of this patent is extended or adjusted under 35 U.S.C. 154(b) by 0 days.

(21) Appl. No.: 11/672,800

(22) Filed: Feb. 8, 2007

(65) Prior Publication Data

US 2008/0194866 A1     Aug. 14, 2008

(51) Int. Cl.
*C07C 51/16*     (2006.01)

(52) U.S. Cl. .................. 562/416; 562/417; 562/412; 562/413

(58) Field of Classification Search ................ 562/416, 562/417, 412, 413
See application file for complete search history.

(56) References Cited

U.S. PATENT DOCUMENTS

| 4,675,438 A | * | 6/1987 | Schwartz et al. ............ 562/416 |
| 5,612,007 A | * | 3/1997 | Abrams ...................... 422/189 |
| 6,562,997 B2 | | 5/2003 | Sikkenga et al. |

* cited by examiner

*Primary Examiner*—Daniel M Sullivan
*Assistant Examiner*—Sudhakar Katakam
(74) *Attorney, Agent, or Firm*—Kelly L. Cummings

(57) ABSTRACT

A process is disclosed for producing at least one high purity aromatic carboxylic acid by oxidizing an aromatic feedstock with oxygen in a reaction medium comprising the aromatic feedstock, a promoter, a heavy metal catalyst, and a solvent which comprises benzoic acid and water to produce a reactor effluent wherein substantially all of the aromatic carboxylic acid produced remains in solution; and then hydrogenating the reactor effluent in the presence of a catalyst and hydrogen. This process efficiently and effectively produces high purity aromatic carboxylic acids by utilizing a common solvent for both oxidation and purification and eliminating the need for intermediate process steps and equipment.

18 Claims, No Drawings

PROCESS FOR THE PRODUCTION OF HIGH PURITY AROMATIC CARBOXYLIC ACIDS USING A BENZOIC ACID AND WATER SOLVENT FOR OXIDATION AND PURIFICATION

FIELD OF THE INVENTION

This invention relates generally to the production of purified aromatic carboxylic acids and, more particularly, to a process for the production of at least one high purity aromatic carboxylic acid using a benzoic acid and water solvent for both oxidation and purification.

BACKGROUND OF THE INVENTION

Terephthalic acid and other aromatic carboxylic acids are widely used in manufacture of polyesters, commonly by reaction with ethylene glycol, higher alkylene glycols or combinations thereof, for conversion to fiber, film, containers, bottles and other packaging materials, and molded articles.

In commercial practice, aromatic carboxylic acids are commonly made by liquid-phase oxidation in an aqueous acetic acid solvent of methyl-substituted benzene and naphthalene feedstocks, in which the positions of the methyl substituents correspond to the positions of carboxyl groups in the desired aromatic carboxylic acid product, with air or another source of oxygen, which is normally gaseous, in the presence of a bromine-promoted catalyst comprising cobalt and manganese. The oxidation is exothermic and yields aromatic carboxylic acid together with byproducts, including partial or intermediate oxidation products of the aromatic feedstock, and acetic acid reaction products, such as methanol, methyl acetate, and methyl bromide. Water is also generated as a byproduct. Aromatic carboxylic acids, typically accompanied by oxidation byproducts of the feedstock, are commonly formed dissolved or as suspended solids in the liquid-phase reaction mixture and are commonly recovered by crystallization and solid-liquid separation techniques.

The exothermic oxidation reaction is commonly conducted in a suitable reaction vessel at elevated temperature and pressure. A liquid-phase reaction mixture is maintained in the vessel and a vapor phase formed as a result of the exothermic oxidation is evaporated from the liquid phase and removed from the reactor to control reaction temperature. The vapor phase comprises water vapor, vaporized acetic acid reaction solvent and small amounts of byproducts of the oxidation, including both solvent and feedstock byproducts. It usually also contains oxygen gas not consumed in oxidation, minor amounts of unreacted feedstock, carbon oxides and, when the oxygen source for the process is air or another oxygen-containing gaseous mixture, nitrogen and other inert gaseous components of the source gas.

The high temperature and pressure vapor phase generated by liquid-phase oxidation is a potentially valuable source of recoverable acetic acid reaction solvent, unreacted feed material and reaction byproducts, as well as energy. However, its substantial water content, high temperature and pressure and corrosive nature due to components such as gaseous methyl bromide, acetic acid solvent and water pose technical and economic challenges to separating or recovering components for recycle and recovering its energy content. Further, impurities that remain unseparated in recovered process streams can prevent re-use of streams if impurities adversely affect other process aspects or product quality.

Purified forms of aromatic carboxylic acids are usually favored for the manufacture of polyesters for important applications, such as fibers and bottles, because impurities, such as the byproducts generated from the aromatic feedstocks during oxidation and, more generally, various carbonyl-substituted aromatic species, are known to cause or correlate with color formation in polyesters made from the acids and, in turn, off-color in polyester converted products.

Preferred purified forms of terephthalic acid and other aromatic carboxylic acids with lower impurities contents, such as purified terephthalic acid or "PTA", are made by catalytically hydrogenating less pure forms of the acids, such as crude product comprising aromatic carboxylic acid and byproducts generated by the liquid-phase oxidation of the aromatic feedstock or so-called medium purity products, in solution at elevated temperature and pressure using a noble metal catalyst. Purification not only removes impurities from the crude and medium purity products, particularly the major impurity, 4-carboxybenzaldehyde, but also reduces the level of color bodies and the amount of metals, acetic acid and bromine in commercial practice, liquid-phase oxidation of alkyl aromatic feed materials to crude aromatic carboxylic acid and purification of the crude product are often conducted in continuous integrated processes in which crude product from liquid-phase oxidation is used as the starting material for purification.

Over time, advances have been made to processes for the production of high purity aromatic carboxylic acids. For instance, benzoic acid has been found to be a viable alternative oxidation solvent since it is relatively resistant to oxidation. U.S. Pat. No. 6,562,997 discloses a process for the production of aromatic dicarboxylic or tricarboxylic acid in which the formation of methyl bromide is substantially reduced relative to conventional processes through the use of benzoic acid as part of the solvent. This reference also teaches that water and benzoic acid are more easily separated due to the differences in their boiling points versus, e.g., water and acetic acid, thereby substantially reducing the complexity of fractionation of the acid and water.

Another notable advance has been the elimination of process steps between oxidation and purification. U.S. Pat. No. 4,675,438 teaches the direct purification of iso- or terephthalic acid products from the oxidation of m- or p-xylene with air in the presence of a combination of bromine with cobalt and manganese and a solvent comprising 85 to 97 percent benzoic acid and 15 to 3 percent water. The direct purification involves diluting the fluid oxidation effluent with water to provide a solvent system of from 25 to 75 weight percent water and from 75 to 25 weight percent benzoic acid, heating the diluted fluid effluent to a temperature at which all of the solids in the oxidation effluent dissolve in the solvent system, and hydrogenating the solution in the presence of a Group VIII noble metal catalyst. Unfortunately, although the low water solvent in the oxidation step facilitates oxidation since water tends to deactivate the catalyst, it does not keep the iso- or terephthalic acid in solution. Therefore, in order to process the oxidation effluent through the hydrogenation step, additional process steps and equipment are still required to add water and heat the effluent to dissolve the iso- or terephthalic acid. This water addition causes the mother liquor from the hydrogenation step to be very high in water content, thereby requiring its subsequent removal in order to maintain the low water solvent in the oxidation step.

Accordingly, it would be desirable to provide a process for the production of at least one high purity aromatic carboxylic acid which not only eliminates the need for intermediate crystallization and solid-liquid separation techniques between the oxidation and purification steps, but also uses the same solvent composition for both oxidation and purification and keeps the aromatic and carboxylic acid in solution through both of these steps. By utilizing the same solvent for both steps, the need to (1) add both water and heat to the oxidation effluent, and thus additional process steps and equipment, in order to dissolve the aromatic carboxylic acid prior to purification and (2) remove water after purification would be eliminated.

SUMMARY OF THE INVENTION

The process of the invention, in its embodiments and features, calls for oxidizing an aromatic feedstock with oxygen in a reaction medium comprising the aromatic feedstock, a promoter, a heavy metal catalyst, and a solvent which comprises benzoic acid and water to produce a reactor effluent wherein substantially all of the aromatic carboxylic acid produced remains in solution; and then hydrogenating the reactor effluent in the presence of a catalyst and hydrogen.

This process efficiently and effectively produces high purity aromatic carboxylic acids by utilizing the common solvent for both oxidation and purification and eliminating the need for intermediate process steps and equipment. Through the use of a common solvent, the present invention in its embodiments also eliminates the need to add both water and heat to the oxidation effluent in order to dissolve the aromatic carboxylic acid prior to purification and the need to remove water after purification.

In one embodiment, the process of the invention also calls for carrying out the oxidation step under reaction conditions which produce a high pressure gaseous stream comprising water, gaseous by-products, and gaseous benzoic acid and further comprising (a.) removing in a separation apparatus at least about 95 weight percent of the benzoic acid from the high pressure gaseous stream to form a second high pressure gaseous stream comprising water and gaseous by-products formed during the oxidation reaction; and (b.) directing at least a part of the second high pressure gaseous stream to a means for recovering energy from the second high pressure gaseous stream.

In another embodiment, this invention provides for carrying out the oxidation step under reaction conditions which produce a high pressure gaseous stream comprising water, gaseous by-products, and gaseous benzoic acid and further comprising directing at least a part of the high pressure gaseous stream to a means for recovering energy from the high pressure gaseous stream.

In a more specific embodiment of the present invention, the process calls for oxidizing paraxylene with oxygen in a reaction medium comprising paraxylene, a promoter, a heavy metal catalyst, and a solvent which comprise from about 60% to about 40% benzoic acid by weight and from about 40% to about 60% water by water to produce a reactor effluent wherein substantially all of the terephthalic acid produced remains in solution; and then hydrogenating the reactor effluent in the presence of a catalyst and hydrogen.

DETAILED DESCRIPTION OF THE INVENTION

The present invention is directed to a process for producing at least one high purity aromatic carboxylic acid. In accordance with this invention, an aromatic feedstock is oxidized with oxygen in a reaction medium comprising the aromatic feedstock, a promoter, a heavy metal catalyst, and a solvent which comprises benzoic acid and water to produce a reactor effluent wherein substantially all of the aromatic carboxylic acid produced remains in solution; and the reactor effluent is then hydrogenated in the presence of a catalyst and hydrogen.

As used herein, "substantially all" means that although minor amounts of solids may be present, the reactor effluent is suitable for feeding to the hydrogenation step without the addition of process steps and equipment, e.g., without the addition of more solvent or heat input to dissolve.

In accordance with one embodiment of this invention, the aromatic feedstocks which may be used include benzene having at least one oxidizable alkyl ring substituent, naphthalene having at least one oxidizable alkyl substituent, and mixtures thereof. Preferable aromatic feedstocks include paraxylene, metaxylene, pseudocumene, orthoxylene, 2,6-dimethylnaphthalene, 1,5-dimethylnaphthalene, 2,7-dimethylnaphthalene and mixtures thereof. Depending upon which aromatic feedstock is utilized, the current invention maybe used to produce terephthalic acid, isophthalic acid, trimellitic acid, phthalic acid, 2,6-naphthalene dicarboxylic acid, 1,5-naphthalene dicarboxylic acid, 2,7-naphthalene dicarboxylic acid or mixtures thereof. When the current invention is used to produce terephthalic acid (TA), the aromatic feedstock is paraxylene. In addition to the preferable aromatic feedstocks listed above, partially-oxidized derivatives of these feedstocks, such as p-toluic acid, p-tolualdehyde, and p-hydroxymethyl benzoic acid, may also be used in the practice of the present invention.

A lower cost feedstock may also be utilized in accordance with this invention by combining paradialkylbenzenes, such as paraxylene, paramethylbenzene, paradiethylbenzene or mixtures thereof, with monoalkylbenzenes, such as toluene, ethylbenzene, propylbenzene or mixtures thereof. The feedstock may contain up to about 10 mole % monoalkylbenzenes, which are converted to benzoic acid during the paradialkylbenzene reaction period, thereby eliminating the need to add "make-up" benzoic acid solvent. Alternatively, a lower cost and lower purity paraxylene feedstock may be utilized in the practice of the present invention to produce lower cost TA. The advantage of using the benzoic acid and water solvent with a feedstock containing, e.g., about 75 wt. % to about 99 wt % paraxylene, with lesser amounts of other C8 aromatic isomers, including metaxylene, orthoxylene and ethylbenzene, is that the ethylbenzene converts to the solvent, thereby eliminating the need for make-up solvent and the difficulty of removal of benzoic acid from the acetic acid and water solvent used in conventional technology. In addition, a high quality TA product can be recovered, as well as a mixture of isophthalic and terephthalic acids, suitable as certain polymer feedstocks, or isophthalic acid and phthalic acid co-products. TA and benzoic acid may also be co-produced in accordance with the present invention by co-oxidizing paraxylene and toluene. The benzoic acid co-product can have many uses, but is preferably converted to phenol by oxidative decarboxylation.

The oxidation catalysts which may be used in the practice of this invention are preferably soluble in the reaction medium to promote contact among catalyst, oxygen and aromatic feedstock, but heterogeneous catalysts or catalyst components may also be used. Typically, the catalyst comprises at lest one heavy metal component such as a metal with atomic weight in the range of about 23 to about 178. Examples include cobalt, manganese, vanadium, molybdenum, chromium, iron, nickel, zirconium, cerium or a lanthanide metal such as hafnium. Preferably, a catalyst comprising one or both of cobalt and manganese is used. Soluble forms of these metals include bromides, alkanoates and bromoalkanoates; specific examples include cobalt acetate and bromide, zirconium acetate and manganese acetate and bromide.

The promoter is used to promote oxidation activity of the catalyst metal, preferably without generation of undesirable types or levels of by-products, and is preferably used in a form that is soluble in the reaction medium. Preferably, the promoter comprises bromine, including elemental, ionic or organic forms thereof. Examples include HBr, NaBr, KBr, $NH_4Br$, bromobenzenes, benzyl-bromide, bromo acetic acid, dibromo acetic acid, tetrabromoethane, ethylene dibromide and bromoacetyl bromide. Other promoters include aldehydes and ketones, such as acetaldehyde and methyl ethyl ketone.

Proportions of the aromatic feedstock, catalyst, oxygen and solvent in oxidation are not critical and vary not only with choice of feed materials and intended product, but also choice of process equipment and operating factors. Oxygen typically is used in at least a stoichiometric amount based on feed, but not so great that unreacted oxygen escaping from the reaction medium to an overhead gas phase forms a flammable mixture with other components of the gas phase. Catalysts suitably are used in weights providing about 100 to about 3000 ppm catalyst metal based on the reactor solvent plus feed weight. Promoter concentrations also generally range from about 100 to about 3000 ppm based on the reactor solvent plus feed weight, with about 0.1 to about 2 milligram-atoms of promoter suitably used per milligram-atom of catalyst metal.

In the practice of the present invention, the benzoic acid and water solvent in oxidation comprises from about 20% to about 80% water by weight. Preferably, the benzoic acid and water solvent comprises from about 40% to about 60% water by weight.

Suitable catalysts used in the hydrogenation step of the current invention may be supported or unsupported. Preferably, the hydrogenation catalyst comprises a relatively high surface area support comprising carbon and one or more metals having catalytic activity for hydrogenation of impurities in impure aromatic carboxylic acid products, such as oxidation intermediates and by-products and/or aromatic carbonyl species. Suitable catalyst metals are the Group VIII noble metals of the Periodic Table of Elements (IUPAC version), including palladium, platinum, rhodium, osmium, ruthenium, iridium, and combinations thereof. Palladium or combinations of such metals that include palladium are most preferred. Suitable metal loadings generally are about 0.1 wt % to about 5 wt % based on total weight of the support and catalyst metal or metals. Preferred catalysts for conversion of impurities present in impure aromatic carboxylic acid products comprising crude terephthalic acid obtained by liquid phase oxidation of a feed material comprising paraxylene contain about 0.1 to about 3 wt % and more preferably about 0.2 to about 1 wt % hydrogenation metal. For such uses, the metal most preferably comprises palladium.

Although the present invention can be carried out as either a batch or continuous process, it is preferred that the process flow move in a continuous mode from the oxidation step to the hydrogenation step. The temperature and pressure conditions are preferably selected in order to maintain the oxidation reaction in the liquid phase. The temperature during the oxidation step should be maintained in the range of about 400° C. to about 500° F. and, preferably, in the range of about 425° F. to about 475° F. The pressure selected for the oxidation step should be at least that which is required to maintain the oxidation reaction in the liquid phase. The temperature and pressure selected for the oxidation step are also maintained during the hydrogenation step. One skilled in the art would recognize that the amount of the benzoic acid and water solvent can be varied to keep the TA in solution at the selected process conditions.

Pure forms of aromatic carboxylic acid product are recovered from the effluent from the hydrogenation step. The hydrogenation reaction effluent, comprising benzoic acid and water solvent having dissolved therein aromatic carboxylic acid and hydrogenated aromatic impurities, is cooled to separate a pure form of solid aromatic carboxylic acid with reduced impurities from the reaction mixture, leaving a liquid purification mother liquor having hydrogenated impurities dissolved therein. Separation is commonly achieved by cooling to a crystallization temperature, which is sufficiently low for crystallization of the aromatic carboxylic acid to occur, thereby producing crystals within the liquid phase. The crystallization temperature is sufficiently high so that dissolved impurities and their reduction products resulting from hydrogenation remain dissolved in the liquid phase. In continuous operations, separation normally comprises removing the effluent from the hydrogenation step and crystallizing the aromatic carboxylic acid in one or more crystallization vessels. When conducted in a series of stages or separate crystallization vessels, temperatures in the different stages or vessels can be the same or different and preferably decrease from each stage or vessel to the next. Crystallization typically also results in flashing of liquid from the effluent from the hydrogenation step, which can be recovered by condensation and recycled to one or more upstream crystallization stages or to the oxidation step.

Thereafter, crystallized, purified aromatic carboxylic acid product is separated from the purification mother liquor, including hydrogenated impurities dissolved therein. Separation of the crystallized product is commonly conducted by centrifugation or filtration. One separation method comprises pressure filtration of a slurry containing pure forms of aromatic carboxylic acid and washing the filter cake that results from filtration with a liquid comprising water as described in U.S. Pat. No. 5,175,355, which is incorporated herein by reference.

The purification mother liquor that remains after recovering the solid purified aromatic carboxylic acid from the effluent from the hydrogenation step comprises water, benzoic acid, promoter, heavy metal catalysts and hydrogenated derivatives of by-products or impurities present in the oxidation reactor effluent. The mother liquor commonly also includes minor amounts of aromatic carboxylic acid that remain in solution. Such hydrogenated derivatives include compounds suitable for conversion to aromatic carboxylic acid by liquid phase oxidation and at least a portion of such hydrogenated derivatives are transferred directly or indirectly to a liquid phase oxidation. Residual aromatic carboxylic acid present in the mother liquid also can be transferred directly or indirectly to liquid phase oxidation after separation from, or together with, such hydrogenated derivatives. Transfer of such derivatives and aromatic carboxylic acid to oxidation is conveniently accomplished by directing at least a portion of a purification mother liquid remaining after separation of a solid pure form of aromatic carboxylic acid to a liquid phase oxidation step.

The oxidation reaction is highly exothermic. The current invention contemplates process conditions in which the reaction medium is allowed to boil, thereby generating a high pressure gaseous stream, which is often an overhead stream. The high pressure gaseous overhead stream comprises water, carbon dioxide, carbon monoxide, benzoic acid, and other oxidation by-products. When the source of oxygen comprises air, the gaseous overhead stream further comprises nitrogen, argon, and other non-condensable inert gases that may be present in the oxygen source.

Treatment of the high pressure gaseous overhead stream may involve directing the high pressure gaseous overhead stream to a separation apparatus in which at least about 95 weight % of the benzoic acid is removed and used in the process, e.g., recycled to the oxidation step or sent to the purification step. Energy may be recovered from a second high pressure gaseous overhead stream from the separation apparatus by directing all or part of it to an energy recovery means, such as an expander or a steam generator. The apparatus used to conduct this separation can be any apparatus that can separate water from the benzoic acid and water solvent, such as a distillation column. Any suitable commercial distillation column may be utilized, including, but not limited to, columns with high-efficiency packing or columns containing sieve, valve, or bubble cap trays. Preferably, the separation apparatus is designed to perform the separation of the water from the benzoic acid and water solvent at elevated pressure. Treatment of the high pressure gaseous overhead stream may alternatively include condensation to recover energy, e.g., by steam generation, with or without fractionation. The energy is efficiently recovered and used, for example, to generate electricity or other forms of useful and transmittable energy.

Energy recovery may also be achieved in the practice of the present invention by removing energy from the reaction medium using a heat transfer apparatus. Such apparatus include, but are not limited to, cooling coils within a reactor, cooling jackets, and heat exchangers. The heat transfer apparatus may be in direct contact with the reaction medium.

The process of the present invention efficiently and effectively produces at least one high purity aromatic carboxylic acid by utilizing a common solvent that is resistant to oxidation for both the oxidation and purification steps, and by eliminating the need for intermediate process steps and equipment. The inventive process is also economically appealing since savings are achieved through reductions in capital and operating costs by adjusting the oxidation and purification conditions to match as closely as possible. Furthermore, the preferred solvent and conditions for both oxidation and purification require little or no manipulation to the oxidation effluent to make it ready for the purification step. Specifically, a solvent containing benzoic acid and at least 20% water significantly improves aromatic carboxylic acid solubility, thereby keeping the aromatic carboxylic acid in solution and allowing both the oxidation and purification steps to be conducted at temperatures as low as about 400° F. Moreover, by keeping substantially all of the aromatic carboxylic acid in solution, energy can be easily and readily recovered from the reaction medium without the formation of solids and subsequently converted to electrical power or other forms of useful and transmittable energy. The use of the benzoic acid and water solvent results in further cost savings since it is less expensive than the conventional acetic acid solvent, as it can also be generated in situ by feeding toluene or other monoalkylbenzenes with the aromatic feedstock.

EXAMPLES

The following examples are intended to be illustrative of the present invention and to teach one of ordinary skill how to make and use the invention. These examples are not intended to limit the invention or its protection in any way.

Example 1

The solubility of TA in a solvent containing 50% benzoic acid and 50% water was determined at various temperatures and is shown below in Table 1.

TABLE 1

| Temp (° F.) | TA Solubility (g TA/100 g Solution) |
|---|---|
| 397 | 5.04 |
| 436 | 8.58 |
| 446 | 9.59 |
| 451 | 9.77 |
| 455 | 10.91 |
| 477 | 13.49 |
| 505 | 18.71 |

Example 2

A 2-liter reactor was charged with 442 g of benzoic acid and 443 g of water. Next, 0.67 g of cobalt(II) in the form of cobalt acetate, 1.86 g of manganese(II) in the form of manganese acetate, and 1.8 g of bromide ion in the form of 48% HBr solution was added to the reactor. The reactor was pressurized (700 psig) with N2 purge, stirred, and heated to approximately the reaction temperature at 455° F. The paraxylene (pX) feedstock flow was initiated at 4.1 g/minute and the gas feed (0.45 standard cubic ft/minute) was changed to 21% O2 to provide the oxidant. After 82 g of pX and about 20-30 g of additional water had been added, the feedstock addition was terminated, the gas low was changed to 8% O2, and the stirring and heating was maintained for an additional 15 minutes to provide a 15-minute period of "post-oxidation".

Table 2 below contains a summary of the oxidation conditions and the analytical results of the products. The "Total Product" was obtained by first drying the total reactor effluent to remove the water and obtain a representative sample of the aromatic components, analyzing the sample by liquid chromatography (LC), then calculating the component concentrations in the reactor at the water/benzoic acid concentrations used in the feedstock. The TA concentration in the reactor of 10.6% for Example 2 is below the solubility of TA given in Example 1 (10.9% at 455° F.) indicating that all of the TA formed was in solution and suitable for direct feeding to the purification step without additional process steps and equipment to dissolve TA solids.

The off-gas from the reaction was continuously monitored for O2, CO, and CO2 content, thus providing the necessary information for burning calculations in Table 2.

The analysis for organic impurities of a sample of the reactor off-gas taken midway through the pX addition period illustrates that the use of the benzoic acid/water solvent system virtually eliminated the formation of methyl bromide, methyl acetate, methane, and other components normally formed by the use of the conventional acetic acid solvent. The calculated total mols of COx/mol of pX fed was 0.34, which indicates that excessive burning of the solvent or feedstock did not occur even at the elevated temperatures of this reaction. Therefore, under the process conditions of this Example, benzoic acid was found to be relatively resistant to oxidation when a solvent containing 50% water was used.

Example 3

Example 3 was conducted as indicated above for Example 2, except that the gas purge during the oxidation step was changed from 21% O2 to pure N2 as soon as all of the pX feedstock had been added, thereby eliminating the post-oxidation step. The conditions and results from Example 3 are listed below in Table 2 and illustrate that a secondary oxidation step is not essential for high levels of pX conversion. The TA concentration in the reactor of 7.77% for Example 3 is below the solubility of TA given in Example 1 (10.9% at 455° F.) indicating that all of the TA formed was in solution and suitable for direct feeding to the purification step without additional process steps and equipment to dissolve TA solids. The formation of only 0.255 mol COx/mol pX illustrates the desirable burning resistance of the solvent and feedstock under these conditions.

TABLE 2

| Oxidation Example # | Post-Oxidation (15 min.) 2 | No Post Oxidation 3 |
|---|---|---|
| | Total Product | Total Product |
| Benzoic acid added (g) | 442.2 | 442.0 |
| Initial Water added (g) | 443 | 443 |
| ppm Co | 753 | 753 |
| ppm Mn | 2106 | 2106 |
| ppm Br | 2049 | 2049 |
| Water added during run (g) | 15-30 | 15-30 |
| pX feed added (g) | 82 | 83 |
| Reactor pressure (psig) | 700 | 700 |
| Air flow rate (scfm) | 0.45 | 0.45 |
| pX Feed Time (min) | 20 | 19 |
| Reaction Conditions | | |
| Primary Oxidation Temp (F.) | 455 | 451 |
| Final Primary Ox PSIG (approx) | 700 | 700 |
| Secondary Ox Temp (F.) | 445 | N/A |
| Secondary Ox PSIG (approx) | 700 | N/A |
| Secondary Ox Time (Minutes) | 15 | N/A |
| LC Results (wt %) | 2-Total Product | 3-Total Product |
| TA | 10.6 | 7.77 |
| 4-carboxybenzaldehyde | 0.11 | 0.74 |
| BENZOIC ACID (BA) | 41.5 | 44.0 |
| p-TOLUIC ACID | 0.19 | 0.71 |
| p-TOLUALDEHYDE | 0 | 0.01 |
| p-XYLENE | 0 | <0.001 |
| | Sum for Total Run | Sum for Total Run |
| Total Run COx Values | | |
| Mol CO/mol pX | 0.030 | 0.017 |
| Mol CO2/mol pX | 0.310 | 0.237 |
| Mol COx/mol pX | 0.340 | 0.255 |
| Average Vent O2 | 1.290 | 1.098 |
| Percent Impurities in Offgas | | |
| Methane | 0.0007 | |
| Methanol | 0.0001 | |

TABLE 2-continued

| Oxidation Example # | Post-Oxidation (15 min.) 2 | No Post Oxidation 3 |
|---|---|---|
| Methyl bromide | <0.00002 | |
| Methyl acetate | <0.00001 | |
| Benzene | 0.0019 | |
| m/p-Xylene | 0.0074 | |

Examples 4 and 5

Examples 4 and 5 were conducted to demonstrate that hydrogenation of the 4-carboxybenzaldehyde (4-CBA) intermediate in the total reactor effluent from the oxidation step occurs in the presence of the benzoic acid, metals, and other oxidation impurities.

To accomplish this, a sample of the dried oxidation total product (which includes the benzoic acid) from Examples 2 and 3, respectively, was charged to a 1 gallon reactor fitted with a basket to contain an aged commercial 0.5% Pd/carbon hydrogenation catalyst. Water was then added to raise the level of the slurry to just below the catalyst basket. The mixed slurry was heated under $N_2$ until the indicated temperature range (the same as used for the oxidation step, i.e., 450-460° F.) was reached. Hydrogen was next charged into the reactor to provide about 100 psi of hydrogen partial pressure. The catalyst basket was then lowered using external controls to contact the mixed liquid, and the hydrogenation was conducted for 4 hours.

Following the 4-hour reaction period, the temperature was reduced, the reactor de-pressurized, and a total product was recovered. The composition of this total product, after removal of most of the water by drying, is shown below in Table 3. The total product contained no detectable 4-CBA, indicating that the hydrogenation catalyst was active for this reaction.

The dried total product from hydrogenation was heated to about 300° F. and hot filtered, then washed with acetic acid to reduce the benzoic acid (simulating high temperature water washing). This treatment produced the "hot filtered cake" obtained from the corresponding total hydrogenated products in Table 3. Thus, Examples 4a and 4b were obtained from the product of Example 2 and Examples 5a and 5b were obtained from the product of Example 3. The results indicate that a TA product free of 4-CBA was obtained with this process.

TABLE 3

| | Example | | | |
|---|---|---|---|---|
| | 4a Dry Total Hydrogenated Product | 4b Hot Filtered Cake | 5a Dry Total Hydrogenated Product | 5b Hot Filtered Cake |
| Feedstock from Example# | 2 | | 3 | |
| Total Oxidation Product (g) | 200 | | 200 | |
| Total Feed (g) | 1320 | | 1320 | |
| Reaction Temperature (° F.) | 450-460 | | 450-460 | |
| Reaction Time (hours) | 4 | | 4 | |
| Metal Analyses (%) | | | | |
| Mn | | <0.0004 | | <0.0004 |
| Co | | <0.0005 | | <0.0005 |
| LC Results (wt %) | | | | |
| Hydroxy methyl benzoic acid | <0.001 | <0.0005 | 0.032 | <0.0005 |

TABLE 3-continued

| | Example | | | |
|---|---|---|---|---|
| | 4a<br>Dry Total<br>Hydrogenated<br>Product | 4b<br>Hot Filtered<br>Cake | 5a<br>Dry Total<br>Hydrogenated<br>Product | 5b<br>Hot Filtered<br>Cake |
| TA | 20.9 | 98.964 | 15.9 | 98.212 |
| 4-CBA | <0.001 | <0.0005 | <0.001 | <0.0005 |
| Benzoic acid | 54.3 | 0.518 | 65.6 | 0.861 |
| p-Toluic acid | 0.376 | 0.066 | 1.72 | 0.529 |
| p-Tolualdehyde | <0.001 | <0.001 | <0.001 | <0.001 |

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claims.

What is claimed is:

1. A process for the production of at least one high purity aromatic carboxylic acid, the process comprising the steps of:
    a. oxidizing an aromatic feedstock with oxygen in a reaction medium comprising the aromatic feedstock, a promoter, a heavy metal catalyst, and a solvent comprising from about 80% to about 20% benzoic acid by weight and from about 20% to about 80% water by weight at a temperature in the range of about 400° F. to about 500° F., thereby producing a reactor effluent wherein substantially all of the aromatic carboxylic acid produced remains in solution; and
    b. hydrogenating the reactor effluent in the presence of a catalyst and hydrogen.

2. The process of claim 1 wherein the aromatic feedstock is selected from the group consisting of benzene having at least one oxidizable alkyl ring substituent, naphthalene having at least one oxidizable alkyl substituent, and mixtures thereof.

3. The process of claim 2 wherein the aromatic feedstock is selected from the group consisting of paraxylene, metaxylene, pseudocumene, orthoxylene, 2,6-dimethylnaphthalene, 1,5-dimethylnaphthalene, 2,7-dimethylnaphthalene and mixtures thereof.

4. The process of claim 3 wherein the aromatic feedstock is paraxylene and the aromatic carboxylic acid is terephthalic acid.

5. The process of claim 1 wherein the promoter comprises bromine.

6. The process of claim 1 wherein the heavy metal catalyst is selected from the group consisting of cobalt, manganese and mixtures thereof.

7. The process of claim 1 wherein the solvent comprises from about 60% to about 40% benzoic acid by weight and from about 40% to about 60% water by weight.

8. The process of claim 1 wherein the hydrogenation catalyst is a Group VIII noble metal catalyst on a carbon support.

9. The process of claim 8 wherein the noble metal is palladium.

10. The process of claim 1 wherein the aromatic feedstock is oxidized at a temperature in the range of about 425° F. to about 475° F.

11. The process of claim 1 wherein the oxidation step is carried out under reaction conditions which produce a high pressure gaseous stream comprising water, gaseous by-products, and gaseous benzoic acid and further comprising:
    a. removing in a separation apparatus at least about 95 weight percent of the benzoic acid from the high pressure gaseous stream to form a second high pressure gaseous stream comprising water and gaseous by-products formed during the oxidation reaction; and
    b. directing at least a part of the second high pressure gaseous stream to a means for recovering energy from the second high pressure gaseous stream.

12. The process of claim 11 wherein the means for recovering energy from the second high pressure gaseous stream comprises an expander.

13. The process of claim 11 wherein the means for recovering energy from the second high pressure gaseous stream comprises a steam generator.

14. The process of claim 1 wherein the oxidation step is carried out under reaction conditions which produce a high pressure gaseous stream comprising water, gaseous by-products, and gaseous benzoic acid and further comprising directing at least a part of the high pressure gaseous stream to a means for recovering energy from the high pressure gaseous stream.

15. The process of claim 14 wherein the means for recovering energy from the high pressure gaseous stream comprises a steam generator.

16. The process of claim 1 wherein energy is removed from the reaction medium using a heat transfer apparatus.

17. The process of claim 16 wherein the heat transfer apparatus is in direct contact with the reaction medium.

18. A process for the production of terephthalic acid comprising the steps of:
    a. oxidizing paraxylene with oxygen in a reaction medium comprising paraxylene, a promoter, a heavy metal catalyst, and a solvent comprising from about 60% to about 40% benzoic acid by weight and from about 40% to about 60% water by weight at a temperature in the range of about 400° F. to about 500° F., thereby producing a reactor effluent wherein substantially all of the terephthalic acid produced remains in solution; and
    b. hydrogenating the reactor effluent in the presence of a catalyst and hydrogen.

* * * * *